United States Patent [19]

Penner

[11] Patent Number: 5,613,503
[45] Date of Patent: Mar. 25, 1997

[54] DEVICE AND METHOD FOR TREATING INGROWING TOE NAILS

[76] Inventor: Abe Penner, 124 Cottonwood Dr., Winkler, Manitoba, Canada, R6W 2A4

[21] Appl. No.: 605,738
[22] Filed: Feb. 22, 1996
[51] Int. Cl.⁶ .................................................. A61F 13/06
[52] U.S. Cl. .......................................... 128/892; 128/893
[58] Field of Search .................................... 128/846, 893, 128/894; 2/21

[56]  References Cited

U.S. PATENT DOCUMENTS

| 592,040 | 10/1897 | Allen | 128/894 |
|---|---|---|---|
| 4,057,055 | 11/1977 | Clark . | |
| 4,068,656 | 1/1978 | Barmore . | |
| 4,674,486 | 6/1987 | Hoffman . | |
| 5,261,872 | 11/1993 | Goldenberg . | |
| 5,394,890 | 3/1995 | Lambert | 128/893 |

FOREIGN PATENT DOCUMENTS 2147211  5/1985  England .

Primary Examiner—Michael A. Brown
Attorney, Agent, or Firm—Adrian D. Battison; Murray E. Thrift

[57] ABSTRACT

A device for reducing the curvature of a toe nail so as to deter ingrowing of the toe nail comprises an upper member and a lower member interconnected by an interconnecting portion interconnecting the members only at the center. The upper member includes an elongate tab which extends rearwardly from a front portion. The front portion of the upper member and the whole of the lower member includes a center section attached to the interconnecting member and a pair of wings which are curved rearwardly and downwardly for engaging the upper and lower surfaces respectively of the nail. The device is held in place by engagement of the wings with the upper and lower surfaces and by the binding of the tab into place on the top of the toe nail with an adhesive bandage.

18 Claims, 2 Drawing Sheets

DEVICE AND METHOD FOR TREATING INGROWING TOE NAILS

BACKGROUND OF THE INVENTION

This invention relates to a device and method for treating ingrowing toe nails which is of a mechanical structure for engaging a forward edge of the toe nail to provide a force for bending the toe nail so as to decrease the curvature of the toe nail and prevent the size of the toe nail from engaging into the flesh of the toe.

Examples of devices of this type are shown in U.S. Pat. Nos. 4,057,055 (Clarke); 4,068,656 (Barmore); 4,647,486 (Hoffman) and 5,261,872 (Goldenberg). Each of these devices provide mechanical elements which engage the toe nail itself and provide a force on the toe nail to modify the curvature thereof.

In addition British patent application 2,147,211 (Johnston) discloses a device comprising a first member which engages over the upper surface of the toe nail adjacent the center and a second portion which engages underneath the lower surface of the toe nail adjacent the sides so as to tend to lift the sides relative to the upper central portion. However a device of this type is ineffective since it tends simply to slip off a nail since there is a force tending to twist the device so that the upper centre part moves forwardly and downwardly allowing it to slip off the forward end of the nail.

SUMMARY OF THE INVENTION

It is one object of the present invention, therefore, to provide an improved device of this general type and to provide an improved method for treating ingrown toe nails using the device.

According to one aspect of the invention there is provided a device for treating ingrowing toe nails comprising: a shaped integral body for engaging the toe nail including: a first member arranged to engage an upper surface of the toe nail adjacent a front edge thereof; a second member arranged to engage an undersurface of the toe nail adjacent the front edge thereof; at an interconnecting portion arranged to extend over the front edge for connecting the first member to the second member; the first member including a front portion arranged to lie adjacent the front edge, to extend across a majority of the width of the front edge and to contact the upper surface of the toe nail adjacent the centre part thereof and to each side of the centre part; the second portion including a front portion arranged to lie adjacent the front edge, to extend across a majority of the width of the front edge and to contact the undersurface of the nail adjacent to center part and to each side of the center part.

One embodiment of the invention will now be described in conjunction with the accompanying drawings in which:

BRIEF DESCRIPTION OF THE DRAWINGS

In the drawings like characters of reference indicate corresponding parts in the different figures.

DETAILED DESCRIPTION

Figure 1:
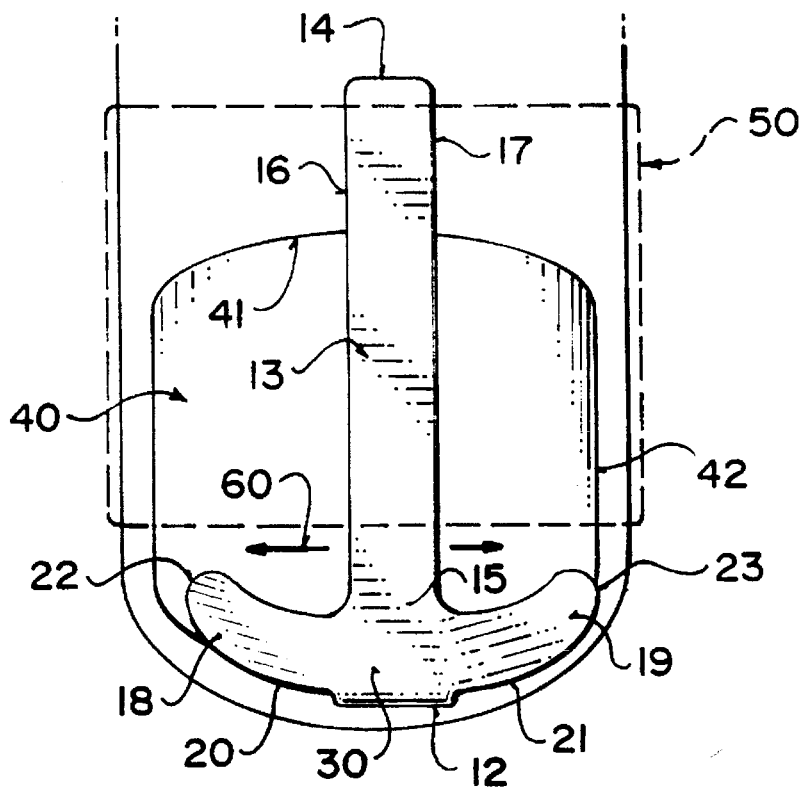
FIG. 1 is a top plan view of the device according to the present invention attached to a toe nail for applying a bending force to the toe nail.
Figure 2:
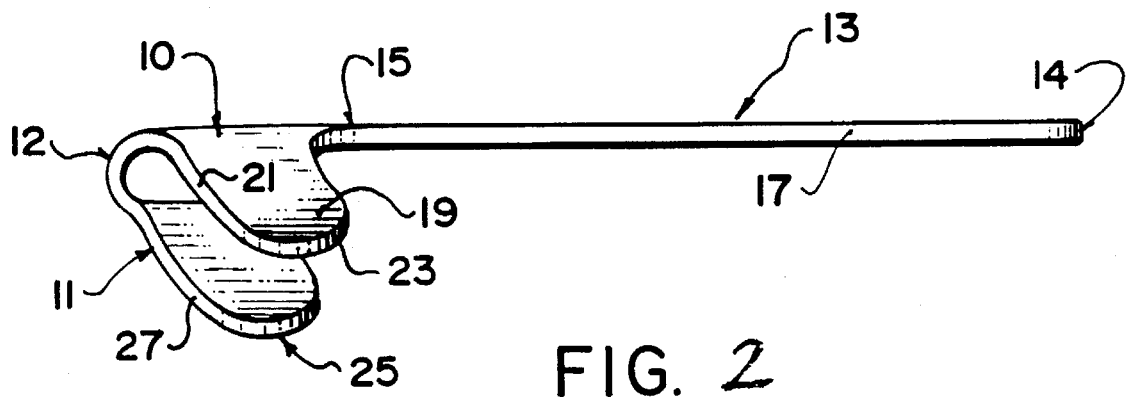
FIG. 2 is a side elevational view of the device of FIG. 1.
Figure 3:
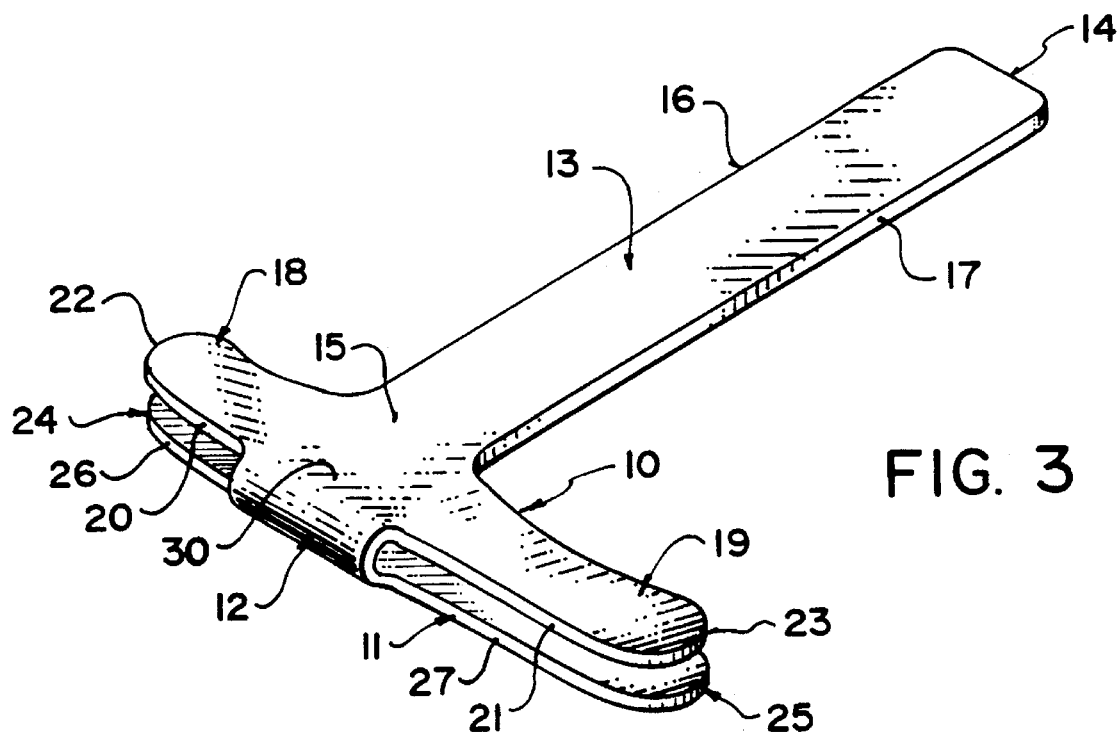
FIG. 3 is an isometric view of the device of FIG. 1.
Figure 4:
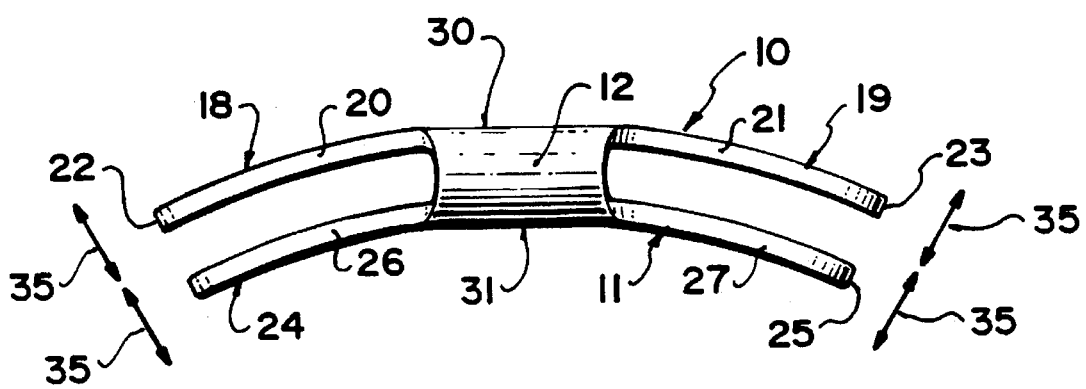
FIG. 4 is a front elevational view of the device of FIG. 1.

The device comprises a first member 10 and a second member 11 with those members being connected by an interconnecting portion 12. The first upper member 10 includes a tab portion 13 which is elongate and relatively narrow extending from a base end 14 to a forward end 15 and having parallel sides 16 and 17. At the forward end of the tab 13 is provided a front portion of the first member 10 which includes a pair of wings 18 and 19 integrally connected with the tab at the forward end 15 thereof. Each of the wings projects out to a respective side of the tab. Each of the wings has a forward edge 20, 21 which curves rearwardly in plan view to an outer edge 22, 23 of the wings.

The second member 11 comprises a pair of wings 24, 25 which are substantially coextensive with and underlie the wings 18 and 19. Thus each of the wings 24 and 25 has a forward edge 26, 27 which curves rearwardly so as to follow the edge 20, 21 in plan view. The interconnecting portion 12 has a width substantially equal to the width of the tab 13 so that the wings are free from the interconnecting portion and project outwardly to each side of the interconnecting portion. The second member 11 is spaced downwardly from the first member 10 by the height of the interconnecting portion 12 and this spacing is of the order of the one to two millimeters so as to leave sufficient space between the first and second members to receive the forward edge of the toe nail therebetween.

The second member between the two wings 24 and 25 extends across the full width of the device so that in effect the front portion of the upper member 10 defines an elongate element which extends across the front edge of the toe nail and contacts the upper surface thereof and similarly the second portion 11 defines an elongate strip for engaging under the front edge of the nail.

As shown in front elevational view, the tab 13 is flat so that the front edge of the upper portion 10 is also flat at the center section 30 so that the wings 18 and 19 curve downwardly from the flat center section. Similarly the centre section 31 of the second or lower member 11 is flat and parallel to the centre section 30 with the wings 24 and 25 being curved downwardly therefrom.

The body defining these elements is formed integrally from a suitable material which is resistant to deformation but can be plastically deformed when bent beyond its resistance so that the curvature of the wings 18, 19 and 24, 25 can be adjusted as indicated by the arrows 35.

As shown in FIG. 1 the width of the device from the outside tips of the wings is slightly less than the width of the toe nail 40. The length of the tab 13 from the interconnecting portion to the rear edge 14 is slightly longer than the length of the nail so that a rear portion of the tab projects beyond the base 41 of the nail.

In operation of the device, the amount of curvature of the wings is adjusted relative to the curvature of the toe nail to which it is to be applied so that the curvature of the wings is less than the curvature of the toe nail, particularly at its side edge 42. In some cases the device will be supplied with a curvature which is suitable, in other cases adjustment can be effected by the user.

With the curvature of the wings thus at the suitable amount, the device is attached to the toe nail by pushing the wings 24 and 25 underneath the front edge of the toe nail while pushing the wings 18 and 19 over the top of the toe nail with the tab 13 lying across the top surface of the toe nail substantially flat against the top surface.

As the width of the device between the outside apexes of the wings is slightly less than the width of the nail, the device can be offset to one side as shown in FIG. 1 so that the wings 19 and 25 engage the side of the nail 42. In this way the center line of the tab is offset to one side from the centre line of the nail. The device is pushed on until the interconnecting portion 12 substantially abuts or is in contact with the front edge of the nail 40. In this position, an adhesive bandage 50 is wrapped around the toe so as to engage over the tab 13 and bind the tab down onto the top surface of the toe.

The length of the tab 13 is so that it is substantially at the base 41 or extends beyond that position. This length of the tab provides an effective engagement of the tab with the top part of the toe so that the device cannot move forwardly from the toe to release the wings from the front edge of the nail, Thus the wings remain in contact with the top surface and bottom surface of the nail respectively and thus hold the nail to follow the curvature of the wings and thus reduce the natural curvature of the nail to reduce the tendency of the nail to ingrow.

The device is thus improved relative to prior art devices by the following important features:

1. The long length of the tab 13 attaches the device to the toe using the adhesive bandage so that the device is attached effectively to the toe and cannot move forward relative to the toe.

2. The upper member 11 includes the side pieces or wings which engage over the top surface of the nail. This again assists in properly locating the device and prevents it from slipping or twisting during the bending action.

3. The bottom or second member 11 includes a piece that goes across the underside of the toe nail so that it is contact with the underside of the toe nail across substantially the full width of the device. This again locates the device more stably on the toe nail and prevents the device from twisting away from the toe nail during the bending action.

It will be appreciated that the amount of force necessary to continuously bend the nail out of its preferred curvature is quite significant and is necessary that the device remain in position in stable condition to maintain this bending action since there is significant tendency for the device to slip and twist if it is only maintained in place by friction.

Once the nail curvature has been reduced by the application of the device to the side 42, the device can be removed and moved across the toe nail as indicated by the arrow 60 to the opposite side of the toe nail to effect a bending action on the toe nail at that side if required.

Since various modifications can be made in my invention as herein above described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. A device for treating ingrowing toe nails comprising:

a shaped integral body for engaging the toe nail including:

a first member arranged to engage an upper surface of the toe nail adjacent a front edge thereof;

a second member arranged to engage an undersurface of the toe nail adjacent the front edge thereof;

and an interconnecting portion arranged to extend over the front edge for connecting the first member to the second member;

the first member including a front portion arranged to lie adjacent the front edge, to extend across a majority of the width of the front edge and to contact the upper surface of the toe nail adjacent a center part thereof and to each side of the center part;

the second member including a front portion arranged to lie adjacent the front edge, to extend across a majority of the width of the front edge and to contact the undersurface of the nail adjacent to the center part and to each side of the center part;

the interconnecting portion being arranged only at the center part so that each of the first and second members includes a pair of wings extending outwardly from the interconnecting portion to each side thereof for contacting the upper and lower surfaces respectively of the nail.

2. The device according to claim 1 wherein each of the wings is plastically deformable.

3. The device according to claim 2 wherein the body is plastically deformable so that the wings can be deformed so as to modify a curvature thereof.

4. The device according to claim 1 wherein each of the first and second members is curved in front elevation so as to define curvatures thereof which are substantially equal.

5. The device according to claim 1 wherein the first member includes a tab portion extending rearwardly from the front portion and is shaped such that the tab portion is narrower than the front portion and the front portion extends out to each side of the tab portion.

6. The device according to claim 5 wherein the tab portion has a length such that it is arranged to extend onto the toe beyond a base of the nail.

7. The device according to claim 1 wherein each of the front portions of the first and second members is arranged to have a width less than the width of the nail so as to be movable on the nail side to side of the nail.

8. The device according to claim 1 wherein the front portion of the first member is substantially coextensive in width to the front portion of the second member.

9. A method for treating ingrowing toe nails comprising:

providing a shaped integral body for engaging the toe nail including:

a first member arranged to engage an upper surface of the toe nail adjacent a front edge thereof;

a second member arranged to engage an undersurface of the toe nail adjacent the front edge thereof;

and an interconnecting portion arranged to extend over the front edge for connecting the first member to the second member;

the first member including a front portion arranged to lie adjacent the front edge, to extend across a majority of the width of the front edge and to contact the upper surface of the toe nail adjacent a center part thereof and to each side of the center part and a tab portion extending rearwardly from the front portion;

the second member including a front portion arranged to lie adjacent the front edge, to extend across a majority of the width of the front edge and to contact the undersurface of the nail adjacent to the center part and to each side of the center part;

engaging the body onto the toe nail with the tab portion extending rearwardly across a top surface of the toe nail and attaching the tab portion to the top surface of the toe nail by an adhesive bandage engaged thereover.

10. The method according to claim 9 wherein the interconnecting portion is arranged only at the center part so that each of the first and second members includes a pair of wings extending outwardly from the interconnecting portion to each side thereof for contacting the upper and lower surfaces respectively of the nail.

11. The method according to claim 10 including deforming each of the wings to adjust a curvature thereof relative to the nail.

12. The method according to claim 9 including curving each of the first and second members in front elevation such that the curvatures thereof are substantially equal.

13. The method according to claim 9 including shaping the first member such that the tab portion is narrower than the front portion and the front portion extends out to each side of the tab portion.

14. The method according to claim 9 including shaping the tab portion with a length such that it is arranged to extend onto the toe beyond the base of the nail.

15. The method according to claim 9 including shaping each of the front portions of the first and second members to be less than the width of the nail and including moving the body on the nail side to side of the nail.

16. The method according to claim 9 including shaping the front portions of the first and second members so as to be substantially coextensive in width.

17. A device for treating ingrowing toe nails comprising:

a shaped integral body for engaging the toe nail including:

a first member arranged to engage an upper surface of the toe nail adjacent a front edge thereof;

a second member arranged to engage an undersurface of the toe nail adjacent the front edge thereof;

and an interconnecting portion arranged to extend over the front edge for connecting the first member to the second member;

the first member including a front portion arranged to lie adjacent the front edge, to extend across a majority of the width of the front edge and to contact the upper surface of the toe nail adjacent a center part thereof and to each side of the center part;

the second member including a front portion arranged to lie adjacent the front edge, to extend across a majority of the width of the front edge and to contact the undersurface of the nail adjacent to the center part and to each side of the center part;

wherein the first member includes a tab portion extending rearwardly from the front portion and is shaped such that the tab portion is narrower than the front portion and the front portion extends out to each side of the tab portion.

18. The device according to claim 17 wherein the tab portion has a length such that it is arranged to extend onto the toe beyond a base of the nail.

* * * * *